(12) United States Patent
Monstadt et al.

(10) Patent No.: US 8,372,110 B2
(45) Date of Patent: Feb. 12, 2013

(54) MEDICAL IMPLANT

(75) Inventors: Hermann Monstadt, Bochum (DE); Hans Henkes, Bochum (DE); Achim Flesser, Mettmann (DE); Ralf Hannes, Dortmund (DE)

(73) Assignee: Covidien LP, Mansfield, MA (US)

( * ) Notice: Subject to any disclaimer, the term of this patent is extended or adjusted under 35 U.S.C. 154(b) by 217 days.

(21) Appl. No.: 12/981,286

(22) Filed: Dec. 29, 2010

(65) Prior Publication Data

US 2011/0098814 A1    Apr. 28, 2011

Related U.S. Application Data

(63) Continuation of application No. 11/575,798, filed as application No. PCT/EP2004/010610 on Sep. 22, 2004, now Pat. No. 7,879,064.

(51) Int. Cl.
*A61M 29/00* (2006.01)
(52) U.S. Cl. ........ 606/200; 606/127; 606/157; 606/191; 623/1.3; 446/491; 446/496; D24/143
(58) Field of Classification Search .................. 606/191, 606/200, 127, 157; 623/1.3–1.33; 446/491, 446/496
See application file for complete search history.

(56) References Cited

U.S. PATENT DOCUMENTS

| | | |
|---|---|---|
| 4,994,069 A | 2/1991 | Ritchart et al. |
| 5,122,136 A | 6/1992 | Guglielmi et al. |
| 5,217,484 A | 6/1993 | Marks |
| 5,234,437 A | 8/1993 | Sepetka |
| 5,261,916 A | 11/1993 | Engelson |
| 5,263,964 A | 11/1993 | Purdy |
| 5,304,194 A | 4/1994 | Chee et al. |
| 5,304,195 A | 4/1994 | Twyford et al. |
| 5,350,397 A | 9/1994 | Palermo et al. |
| 5,354,295 A | 10/1994 | Guglielmi et al. |
| 5,423,829 A | 6/1995 | Pham et al. |
| 5,443,478 A | 8/1995 | Purdy |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,582,619 A | 12/1996 | Ken |
| 5,624,449 A | 4/1997 | Pham et al. |
| 5,624,461 A | 4/1997 | Mariant et al. |
| 5,639,277 A | 6/1997 | Mariant et al. |
| 5,645,558 A | 7/1997 | Horton |
| 5,649,949 A | 7/1997 | Wallace et al. |
| 5,658,308 A | 8/1997 | Snyder |
| 5,690,667 A | 11/1997 | Gia |
| 5,749,891 A | 5/1998 | Ken et al. |
| 5,766,219 A | 6/1998 | Horton |
| 5,851,206 A | 12/1998 | Guglielmi et al. |
| 5,853,418 A | 12/1998 | Ken et al. |
| 5,855,578 A | 1/1999 | Guglielmi et al. |
| 5,891,128 A | 4/1999 | Gia et al. |
| 5,891,130 A | 4/1999 | Palermo et al. |
| 5,895,385 A | 4/1999 | Guglielmi et al. |
| 5,895,391 A | 4/1999 | Farnholtz |
| 5,911,731 A | 6/1999 | Pham et al. |
| 5,916,235 A | 6/1999 | Guglielmi et al. |

(Continued)

*Primary Examiner* — Gary Jackson
*Assistant Examiner* — Keivn Everage
(74) *Attorney, Agent, or Firm* — Elizabeth A. O'Brien, Esq.

(57) ABSTRACT

The invention relates to a medical implant in the form of an elongated helix wherein at least one part of the helix is preformed in such a manner that it has a secondary structure of identically sized loops which it assumes during implantation at the placement site, with said structure in turn forming at the placement site during implantation a polyhedral tertiary structure, and the polyhedron being provided with at least one additional loop.

11 Claims, 8 Drawing Sheets

U.S. PATENT DOCUMENTS

| | | | |
|---|---|---|---|
| 5,919,187 | A | 7/1999 | Guglielmi et al. |
| 5,925,037 | A | 7/1999 | Guglielmi et al. |
| 5,928,226 | A | 7/1999 | Guglielmi et al. |
| 5,935,145 | A | 8/1999 | Villar et al. |
| 5,941,888 | A | 8/1999 | Wallace et al. |
| 5,944,714 | A | 8/1999 | Guglielmi et al. |
| 5,947,962 | A | 9/1999 | Guglielmi et al. |
| 5,947,963 | A | 9/1999 | Guglielmi |
| 5,957,948 | A | 9/1999 | Mariant |
| 5,976,126 | A | 11/1999 | Guglielmi et al. |
| 5,984,929 | A | 11/1999 | Bashiri et al. |
| 6,010,498 | A | 1/2000 | Guglielmi |
| 6,013,084 | A | 1/2000 | Ken et al. |
| 6,033,423 | A | 3/2000 | Ken et al. |
| 6,063,070 | A | 5/2000 | Eder |
| 6,063,100 | A | 5/2000 | Diaz et al. |
| 6,066,133 | A | 5/2000 | Guglielmi et al. |
| 6,066,149 | A | 5/2000 | Samson et al. |
| 6,077,260 | A | 6/2000 | Wheelock et al. |
| 6,083,220 | A | 7/2000 | Guglielmi |
| 6,090,125 | A | 7/2000 | Horton |
| 6,102,932 | A | 8/2000 | Kurz |
| 6,123,714 | A | 9/2000 | Gia et al. |
| 6,136,015 | A | 10/2000 | Kurz et al. |
| 6,146,373 | A | 11/2000 | Cragg et al. |
| 6,156,061 | A | 12/2000 | Wallace et al. |
| 6,159,165 | A | 12/2000 | Ferrera et al. |
| 6,165,178 | A | 12/2000 | Bashiri et al. |
| 6,171,326 | B1 | 1/2001 | Ferrera et al. |
| 6,190,373 | B1 | 2/2001 | Palermo et al. |
| 6,193,728 | B1 | 2/2001 | Ken et al. |
| 6,221,066 | B1 | 4/2001 | Ferrera et al. |
| 6,231,586 | B1 | 5/2001 | Mariant |
| 6,254,592 | B1 | 7/2001 | Samson et al. |
| 6,280,457 | B1 | 8/2001 | Wallace |
| 6,319,267 | B1 | 11/2001 | Kurz |
| 6,322,576 | B1 | 11/2001 | Wallace et al. |
| 6,344,041 | B1 | 2/2002 | Kupiecki et al. |
| 6,371,972 | B1 | 4/2002 | Wallace et al. |
| 6,383,174 | B1 | 5/2002 | Eder |
| 6,383,204 | B1 | 5/2002 | Ferrera et al. |
| 6,425,893 | B1 | 7/2002 | Guglielmi |
| 6,468,266 | B1 | 10/2002 | Bashiri et al. |
| 6,478,773 | B1 | 11/2002 | Gandhi et al. |
| 6,485,524 | B2 | 11/2002 | Strecker |
| 6,511,468 | B1 | 1/2003 | Cragg et al. |
| 6,544,275 | B1 | 4/2003 | Teoh |
| 6,551,340 | B1 | 4/2003 | Konya et al. |
| 6,558,367 | B1 | 5/2003 | Cragg et al. |
| 6,585,754 | B2 | 7/2003 | Wallace et al. |
| 6,605,101 | B1 | 8/2003 | Schaefer et al. |
| 6,607,538 | B1 | 8/2003 | Ferrera et al. |
| 6,616,617 | B1 * | 9/2003 | Ferrera et al. ............... 600/585 |
| 6,620,152 | B2 | 9/2003 | Guglielmi |
| 6,635,069 | B1 | 10/2003 | Teoh et al. |
| 6,638,291 | B1 | 10/2003 | Ferrera et al. |
| 6,656,201 | B2 | 12/2003 | Ferrera et al. |
| 6,679,903 | B2 | 1/2004 | Kurz |
| 6,860,893 | B2 | 3/2005 | Wallace |
| 6,929,654 | B2 | 8/2005 | Teoh et al. |
| 6,964,657 | B2 | 11/2005 | Cragg et al. |
| 6,966,892 | B2 | 11/2005 | Gandhi et al. |
| 7,147,618 | B2 | 12/2006 | Kurz |
| 7,198,613 | B2 | 4/2007 | Gandhi et al. |
| 7,238,194 | B2 | 7/2007 | Monstadt et al. |
| 7,300,458 | B2 | 11/2007 | Henkes et al. |
| 7,316,701 | B2 | 1/2008 | Ferrera et al. |
| 7,323,000 | B2 | 1/2008 | Monstdt et al. |
| 7,524,322 | B2 | 4/2009 | Monstadt et al. |
| 7,575,582 | B2 | 8/2009 | Gandhi et al. |
| 7,578,826 | B2 | 8/2009 | Gandhi et al. |
| RE41,029 | E | 12/2009 | Guglielmi et al. |
| 7,879,064 | B2 | 2/2011 | Monstadt et al. |
| 2002/0019647 | A1 * | 2/2002 | Wallace et al. ............... 606/200 |
| 2003/0014073 | A1 | 1/2003 | Bashiri et al. |
| 2003/0040733 | A1 | 2/2003 | Cragg et al. |
| 2003/0225365 | A1 | 12/2003 | Greff et al. |
| 2004/0045554 | A1 | 3/2004 | Schaefer et al. |
| 2005/0079196 | A1 | 4/2005 | Henkes et al. |
| 2006/0036281 | A1 | 2/2006 | Patterson et al. |
| 2008/0045922 | A1 | 2/2008 | Cragg et al. |
| 2008/0051803 | A1 | 2/2008 | Monjtadt et al. |
| 2008/0103585 | A1 | 5/2008 | Monstadt et al. |
| 2008/0125855 | A1 | 5/2008 | Henkes et al. |
| 2008/0228215 | A1 | 9/2008 | Strauss et al. |
| 2008/0228216 | A1 | 9/2008 | Strauss et al. |
| 2009/0254111 | A1 | 10/2009 | Monstadt et al. |
| 2010/0023105 | A1 | 1/2010 | Levy et al. |
| 2010/0030200 | A1 | 2/2010 | Strauss et al. |
| 2010/0049165 | A1 | 2/2010 | Sutherland et al. |
| 2010/0076479 | A1 | 3/2010 | Monstadt |

* cited by examiner

MEDICAL IMPLANT

CROSS-REFERENCE TO RELATED APPLICATIONS

This application is a continuation of U.S. application Ser. No. 11/575,798, filed May 1, 2008, which is incorporated in its entirety by reference, herein, and which is a national phase application of International Application No. PCT/EP2004/010610, filed on Sep. 22, 2004 and published in German on Mar. 30, 2006 as WO 2006/032289 A1, which is incorporated in its entirety by reference, herein.

BACKGROUND

1. Field of the Invention

The invention relates to a medical implant in the form of an elongated helix wherein at least one part of the helix is preformed in such a manner that it has a secondary structure which it assumes during implantation at the placement site, with said structure in turn forming at the placement site during implantation a polyhedral tertiary structure, with each face of the polyhedron being built up by a loop.

The invention, furthermore, relates to a device for the implantation of such implants in body cavities and vessels.

2. Description of the Related Art

Known in the art is the use endovascular techniques for the occlusion of body cavities or vessels such as arteries, veins, fallopian tubes or vascular deformities such as, for example, vascular aneurysms. In this case, the closure element (also termed occlusion means) is usually introduced by means of an insertion aid through a catheter into the cavity to be occluded and deposited therein by means of one of various known techniques. The occlusion of the cavity finally is brought about by an embolus that forms as a result of the flow of blood slowing down in the cavity thus reduced in size or filled by the occlusion means.

It is furthermore known in the art to introduce a plurality of filamentous occlusion means, for the most part helixes or spirals of stainless steel or platinum alloys, into vascular aneurysms, with said means then assuming a random configuration and in this way occlude the aneurysm. The drawback of such a method is that the occlusion means often fill and stabilize the cavity only inadequately and it is quite difficult to foresee the behavior of said means when assuming their superimposed structures so that in the end the safety of the operation may be at risk as a 'stiletto effect' cannot be ruled out and may even entail wall ruptures.

SUMMARY OF THE INVENTION

In order to circumvent such disadvantages it is furthermore known to make use of occlusion means made of shape memory materials, said means assuming a defined secondary and/or tertiary structure when inserted into the cavity to be occluded.

With a view to most effectively filling vascular aneurysms and at the same time stabilizing the aneurysm wall it is thus known in this context from WO 01/93937 to use an occlusion means made of a material having shape memory properties, said means when inserted having the primary form of an elongated filament that upon being inserted into the aneurysm to be occluded develops into a secondary structure forming six loops of identical size which together build up a three-dimensional tertiary structure having the form of a cage or cube. Each of the loops thus forms a face of the spatial structure and in this way determines the size of the structure.

This principle is also known from WO 03/017852 which provides for implants that as soon as external constraints are removed assume a regular, meander-like secondary structure which in turn develops into a spatial tertiary structure taking for example the form of a geometric cage, cube, tetrahedron or prism.

Occlusion means of this kind are meant to stabilize the aneurysm wall so that further filamentous occlusion means can be inserted subsequently without running the risk of causing wall ruptures. Although such occlusion means may be viewed as an improvement compared to non-preformed occlusion means in that they provide increased safety of operation, imminent rupturing danger still exists however in areas of the aneurysm wall, in particular those adjacent to faces and vertices as well as edges of the polyhedrons, especially as a result of the occlusion helixes subsequently inserted into the aneurysm. Moreover, because of the largely openly configured tertiary structure of such occlusion means the subsequently inserted occlusion means or portions of such occlusion means can only be prevented from exiting through the neck of the aneurysm primarily in the case of small-neck aneurysms.

In view of the disadvantages associated with the state of the art it is thus the object of the invention to provide an implant that further reduces risks for patients when body cavities and vessels have to be occluded. Desirable characteristics in this context are an extensive and dense coverage of the wall of the aneurysm, close contact with the aneurysm wall, a reliable occlusion of the aneurysm neck and/or prevention of the 'stiletto effect'.

According to the invention this objective is reached by providing a medical implant of the kind first mentioned above which is characterized in that the polyhedron is provided with at least one additional loop.

The invention is based on findings proving that when a higher packing density of the polyhedron is achieved through the provision or arrangement of additional loops the wall rupturing risk diminishes without the maneuverability of the implant during placement being impaired significantly. Preferably, the additional loops have a slightly smaller diameter than the loops building up the faces of the polyhedron.

In this case, the implant is preformed in such a manner that it assumes the desired secondary and tertiary structure after it has been released from the constraints of the catheter. For this purpose, an elastic biasing force is imprinted on the helix, but at least on the portion that forms the polyhedron, in a manner known through prior art techniques. Therefore, not before an external (thermal or mechanical) constraint is omitted does the implant abandon its elongated structure and forms into its predetermined three-dimensional tertiary structure. Such a mechanical constraint, for example, may be exerted by the catheter or a retaining element embracing or being situated within the helix. The thermal constraint may, for instance, be imposed by temperature conditions prevailing in the catheter that differ from those encountered in the blood stream. Means and interrelations of this kind are sufficiently known to competent persons skilled in the art.

With aid of inventive implants preformed in the described manner it is possible to achieve a dense and gentle filling of the cavity to be occluded without the wall of the cavity having to serve as an abutment when the desired three-dimensional structure is formed, which is the case with non-preformed implants. The risk of causing wall ruptures can thus be minimized.

Especially suited for the creation of such an elastic biasing force are materials having shape memory characteristics or materials having superelastic properties which are capable of undergoing a temperature- or stress-induced martensitic transformation or a combination of both. Other materials lacking shape memory properties such as, for example, platinum alloys, especially platinum-iridium and platinum-tungsten alloys, also lend themselves to the formation of the inventive implants.

In this context the additional loop or further loops may be arranged in the polyhedron on one or several faces of the polyhedron. For example, one or also several smaller sized loop(s) may thus be arranged within a face of the polyhedron formed by a larger loop. This leads to a denser packing of the polyhedron faces and minimizes the risk of the adjacent vessel or aneurysm walls becoming ruptured through additionally inserted filamentous occlusion means. Furthermore, the neck of the aneurysm can be better occluded in this way so that there is lower risk that additionally inserted filamentous occlusion means may exit.

The additional loop or further loops may also be arranged on the edges of the polyhedron to enable the polyhedron edges to become more densely packed which yields the advantages referred to above with respect to adjacent aneurysm areas.

Moreover, the additional loop or further loops may be arranged in areas of the vertices of the polyhedron to enable these vertex locations to become more densely packed which also yields advantages as described hereinbefore with respect to adjacent aneurysm areas.

The three above elucidated possibilities of arranging further loops are not necessarily facultatively with embodiments featuring more than one additional loop but may also be adopted in a cumulative manner to create packings of the polyhedron that are optimally adapted to the cavity to be occluded. The objective in this way is to obliterate the neck of the aneurysm to prevent the spirals from being flushed out.

As per an expedient embodiment of the inventive implant the polyhedron is a regular or a semi-regular polyhedron. In the event of a semi-regular polyhedron the faces themselves are also built up by differently sized loops. Furthermore, loops of even smaller size may be arranged within the smaller polyhedron faces formed by smaller loops so that the relevant faces can be provided with a denser packing. The above described steps aimed at achieving a denser packing in the areas of vertices and/or edges may expediently be adopted in this case as well.

It is seen as particularly expedient here if the polyhedron is a tetrahedron, a hexahedron (preferably a cube), an octahedron, a dodecahedron or an icosahedron. In the framework of the present invention a tetrahedron is especially preferred.

The loops may be provided in the form of closed or open loops. In a closed loop the proximal and distal ends of the filament portion forming the closed loop intersect whereas such intersection or crossing does not take place in open loops. Because of the increased stability of the tertiary structure formed by the loops it is considered advantageous if at least one and preferably all of the loops are closed loops.

According to another preferred embodiment the size relation between small and large loops ranges between 1:1.1 and 1:5, preferably 1:1.1 and 1:4 and especially preferred 1:1.1 and 1:2. The sizing depends, inter alia, on the arrangement of the loops at the faces/edges or vertices. The implant in this case may consist of loops of two or more different sizes. If two loops are arranged on one face the size relation as a rule ranges between 1:1.1 and 1:2 with the diameter serving as reference dimension.

As per another preferred embodiment the implant comprises more than one smaller loop. Particularly preferred in the interest of increasing the safety of operations by providing a higher packing density is a numerical relation between smaller and larger loops of at least 1:1.

With a numerical relation between smaller and larger loops of 1:1 it is preferred if the small and large loops are alternately arranged along the linear extension of the filament. This arrangement results in the safety of the treatment being further enhanced because it greatly improves the maneuverability and, surprisingly, enables the implanted filament to be partially retracted from the cavity and into the catheter for repositioning purposes during placement without canting, knots or failure of the filament occurring.

In accordance with an especially preferred embodiment a smaller closed loop is arranged in the polyhedron in each of the polyhedron faces formed by the large loops.

It is, furthermore, particularly beneficial if in the polyhedron between each of two adjacent loops forming the faces at least one smaller loop each (or may be even more loops) is arranged. The loops arranged between each of two adjacent loops forming the faces of the polyhedron are situated on the edges of the polyhedron in this case.

Moreover, it is especially advantageous if in all areas of the polyhedron where in each case at least three the faces forming loops adjoin at least one small loop each is arranged (or may be even more loops). The loops arranged between each of at least three adjacent loops forming the faces of the polyhedron are situated on the vertices of the polyhedron in this case.

It is, moreover, particularly expedient if the polyhedron is a tetrahedron, the faces of which being formed by one of the large loops each, with one smaller loop being located in each larger loop in this case as well.

As per another preferred embodiment the polyhedron is a tetrahedron, the faces of which being formed by one of the large loops each, with one smaller loop being located between each of two large loops at one edge of the tetrahedron each.

A preferred further embodiment relates to an inventive medical implant wherein the polyhedron is a tetrahedron, the faces of which being formed by one of the large loops each, with one smaller loop being located between each of three large loops at one vertex of the tetrahedron.

For the purpose of occluding aneurysms it is seen particularly expedient to use implants according to the invention, the polyhedrons of which have a diameter ranging between 0.5 and 30, preferably 1 and 25 and especially preferred between 2 and 20 and in particular between 3 and 18 mm.

It is furthermore advantageous if the polyhedron is of larger size than the volume of the body cavity (the so-called "therapeutic space") for the filling of which it is meant. This so-called 'oversizing' serves to stabilize the implant in the cavity to be occluded and in this way prevents it from being displaced within or expelled in part or completely from the cavity. However, to prevent the thin-walled aneurysms from being ruptured it is nevertheless deemed expedient not to provide for too great a size of the polyhedron in relation to the relevant therapeutic space. It is therefore considered beneficial if the diameter of the polyhedron is not sized greater than 2.5, preferably 1.1 to 2 and especially preferred 1.2 to 1.5 times the diameter of the body cavity it shall fill.

The implant according to the invention is thus particularly suited for the occlusion of aneurysms having a therapeutic measure (that is a diameter) ranging between 0.4 and 40, preferably between 1.5 and 20 and in particular between 2 and 18 mm.

According to an expedient embodiment the filament (if only a portion of the filament is used to form the polyhedron than particularly this portion) in its extended state has a length of between 50 and 600 and preferably between 75 and 500 mm.

The inventive implant may comprise, for example, of a helix or spiral formed by means of at least a single wire or with the aid of a cable-like structure formed by means of at least two wires. Configurations in the form of a helix or spring or cable-like structure thus offer advantages in that an enlarged surface is provided for thrombozation purposes. To achieve the same purpose further configurations of the helix can be put to use that are conducive to a surface enlargement, for example providing said helix with fibers promoting the formation of thrombi.

The single or plurality of wires in this case expediently have a diameter ranging between 20 and 200, preferably between 30 and 100, especially preferred 50 and 70 and in particular between 55 and 65 .mu.m.

In accordance with an expedient embodiment the helix or spiral has an internal lumen that is closed off at least at the distal end. At the proximal end the lumen may be open or closed. A lumen open towards the proximal end is, for instance, expedient if a removable retaining element is arranged in the inner lumen of the filament, said element preventing the previously imprinted secondary and tertiary structure to be assumed as long as it is located inside the implant. Such a retaining element has been disclosed via publication WO 03/041615, with express reference being made here to its disclosure content.

It is, furthermore, expedient if the helix has an outer diameter of between 0.1 and 0.5, preferably between 0.2 and 0.35 and especially preferred between 0.24 and 0.28 mm. The helix in this case is preferably designed as micro-helix or micro-spring comprising one or several wires or as a cable-like structure consisting of more than one wire braided or twisted together.

As per a further expedient embodiment at least one of the wires forming the helix or the wire forming the helix is made of a platinum alloy, preferably a platinum-iridium or a platinum-tungsten alloy or a metal alloy having shape memory properties.

It may be expedient if a filamentous shaping element made of a metal alloy having shape memory properties passes through the helix along its longitudinal axis. The shaping element serves to bring about the secondary and tertiary structure of the implant having left the catheter. In this embodiment the filament having been released from the catheter adapts to the predetermined shape of the shaping element which enables the envisaged three-dimensional tertiary structure to be formed. Such a shaping element, for example, has been disclosed in publication WO 03/017852, with explicit reference being made here to its disclosure content.

This embodiment provides for the helix to be expediently designed as cable comprising several wires, one of which being the shaping element, and, especially preferred, as spiral or helix through which inner lumen the shaping element, preferably a wire, extends. It is, furthermore, considered expedient with this embodiment if the spiral or helix or, in case the design provides for a cable, those parts of the cable which do not form the shaping element, are made of a material that does not have shape memory properties. Particularly expedient in this case is a platinum-iridium alloy.

The alloy having shape memory properties in this case is preferably a titanium- and nickel-containing alloy (also known under the name of nitinol), an iron-based or copper-based alloy.

According to another preferred embodiment the filamentous shaping element extending along the longitudinal axis of the helix has a tapered portion situated in its distal end area. In this area said shaping element thus has a diameter smaller than the element diameter in proximal direction. Such a distal tapered portion causes the shaping element to be softer and less stiff so that traumatizing risks are less imminent in the event the distal end of the shaping element comes into contact with the wall of the aneurysm. Said distally arranged tapered section is provided because it was found that the total stiffness of a helix through which a filamentous shaping element extends is for the main part due to the shaping element and only to a lesser extent to the helix itself. The taper may, for example, extend from the distal tip over a length of approx. 20 mm and may have an incremental slope, but preferably a continuous slope. All in all, the diameter of the shaping element up to its distal tip preferably reduces to approx. 25 to 50% of the diameter existing in the remaining area.

Another expedient embodiment relates to an inventive medical implant wherein a filamentous retaining element made of a polymer material (in particular a polyester or polyamide) or a metal wire without shape memory properties (in particular a medical stainless steel wire) passes through the helix along its longitudinal axis. The retaining element in this case serves to maintain the elongated configuration (in this case the retaining element expediently is made and consists of a metal wire, especially in combination with a helix made of a shape memory material) or secure the helix preventing it from being torn off during placement, in particular when repositioning is required. In the latter case, provision of the retaining element made of a polymer material and of the helix made of a shape memory material or a platinum-tungsten alloy is deemed particularly expedient. Because of its good supporting qualities instrumental in improving the slidability of the implant using a platinum-tungsten alloy material for the helix is especially preferred.

The present invention, furthermore, relates to a device for the placement of implants into body vessels and cavities with an implant in accordance with the invention and an insertion aid which is detachably connected to the proximal end of the implant.

The insertion aid in this case is preferably designed as a guide wire which expediently and at least in part has the form of a helix or spring. The dimensioning and selection of suitable materials is sufficiently known to competent persons skilled in the art. For this purpose and by way of example explicit reference is made to the disclosure content of publications WO 03/017852 and WO 03/041615.

If the inventive implant is provided with a removable retaining element it has, expediently, the form of an open tube through which the retaining element can be introduced in and removed from the implant.

For the purpose of placing the implant into the cavity to be occluded implant and insertion aid are expediently connected with each other by means of a severance module. For electrolytic placement of the implant the severance module is expediently provided with an electrolytically corrodible spot made of a suitable material, for example a corrodible steel alloy.

Moreover, in the implant according to the invention one or more additional severance modules may be provided and arranged in the helix proximal to the portion forming the polyhedron. This enables the inner hollow space of the polyhedron to be filled immediately after it has been placed into the body cavity to be occluded. The filament segment arranged between polyhedron and severance module may be elastically preformed itself so that it is capable of assuming or taking up a defined form or position within the polyhedron. Arranging several severance modules of this kind inside the helix enables helix segments that can be variably sized to be introduced into the polyhedron lumen. For electrolytic placement of the implant the severance module is expediently provided with an electrolytically corrodible spot or location.

It is also viewed expedient if the device in accordance with the invention also comprises a catheter, a voltage source and a cathode, with the implant serving as anode and being longitudinally movable in the catheter, and with the connection between implant and insertion aid (preferably the severance module) having an electrolytically corrodible location so that the implant can be detached by electrolytic processes when in contact with a body fluid.

In the interest of high resistance against fracture or breaking and at the same time aiding the detachment process the severance module has a diameter ranging between 30 and 150, preferably between 40 and 120 and especially preferred between 50 and 100 .mu.m. The electrolytically corrodible location in this case may have a smaller diameter than the adjacent proximal and distal areas of the severance module (the severance module in this case tapers off towards the electrolytically corrodible spot).

The severance module is expediently provided with a proximal and a distal helix as well as a segment arranged in between, with the helixes consisting of a material whose susceptibility to electrolytic corrosion is lower than that of the interposed segment. Suitable and expedient material combinations are noble metals or noble metal alloys, preferably platinum or platinum alloys for the proximal helix or distal helix and stainless steel (e.g. grades AISI 301, 303 or 316 as well as subgroups thereof or N-alloyed austenitic steel of stainless quality grade, preferably from the group of pressure-nitrided steels) for the interposed segment. Material combinations of this type are also known from WO 03/017852 to which reference is made here.

In accordance with an advantageous embodiment of the inventive device the severance module is non-detachably connected to the implant and the insertion aid by welding, soldering, bonding or mechanical joining processes, particularly by force- or form-closing methods in a manner known to persons skilled in the art.

As per another advantageous configuration of the inventive device the insertion aid is surrounded, at least in part, by an electrically insulating shrunk-on sleeve or an electrically insulating coating.

Moreover, the purpose of the invention can be most beneficially accomplished with the aid of a helix, the loops of which forming the faces of a dodecahedron, in particular a regular pentagonal dodecahedron. Due to the plurality of faces—twelve altogether—a very dense coverage of the wall is achieved so that, as the case may be, even without additional loops the aneurysm wall can be widely covered and an extensive obliteration of the neck of the aneurysm be brought about.

The helix designed and preformed so as to yield the shape of a pentagonal dodecahedron thus forms a flexible skeleton covering and protecting the wall, with said skeleton being capable of accommodating and retaining further helixes serving occlusion purposes. In this case further loops often need no longer be arranged additionally on faces, edges or vertices. In this respect, measures promoting the sliding behavior aimed at counteracting patient traumatizing risks can largely be dispensed with.

Arranging the proximal end of the helix forming the pentagonal dodecahedron on a vertex or corner point was found to be particularly beneficial. Since the neck of the aneurysm is usually located within a face of the polyhedron this makes it difficult for the last-inserted portion of the helix to slip out of the neck and helps to prevent the helix from being flushed out which anyway is improbable due to the plurality of the faces, the close contact with the wall of the aneurysm and the strain that as a rule prevails inside the aneurysm. The distal end of the helix is preferably arranged in a face and is the point where the first loop starts; advantageously here is a mainly atraumatic supporting location on a side facing away from the neck of the aneurysm.

BRIEF DESCRIPTION OF THE DRAWINGS

The invention is now described by way of examples as follows with reference being made to the figures showing the respective embodiments.

DETAILED DESCRIPTION

Figure 1:
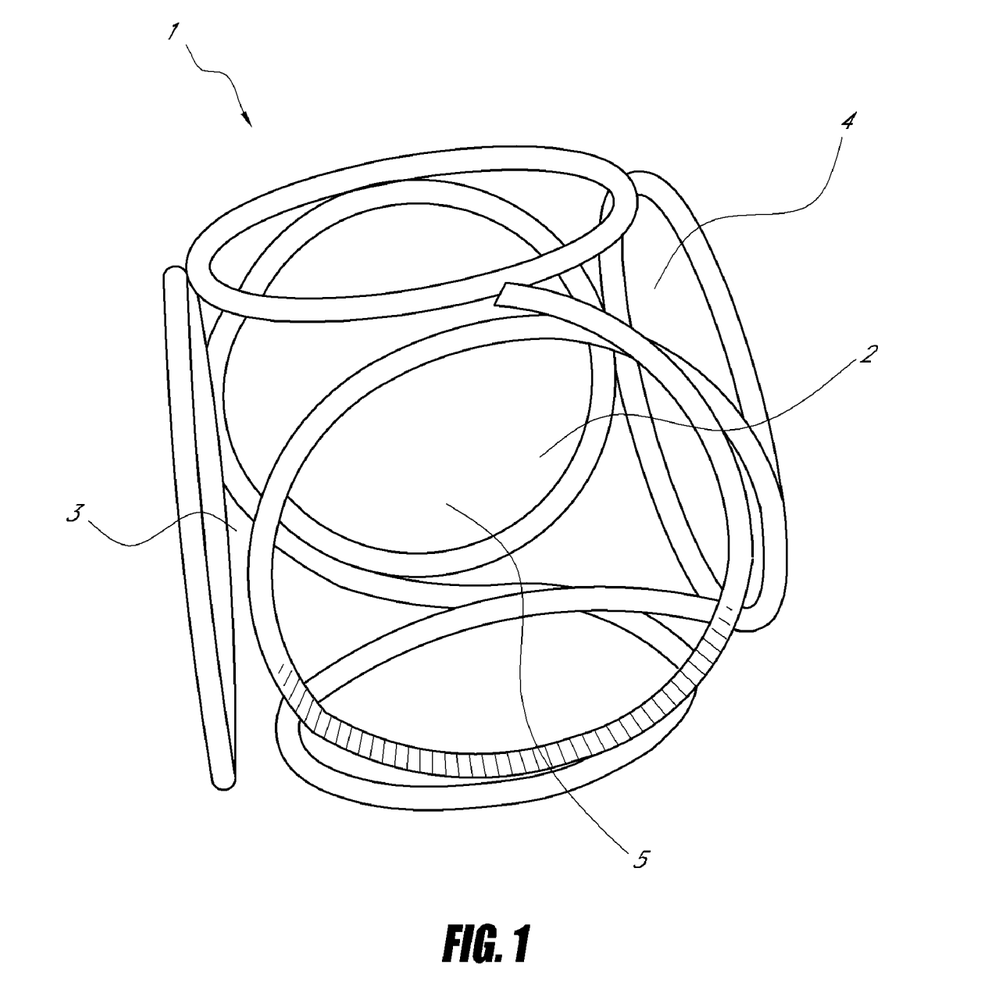
FIG. 1 shows the enlarged representation of a cube-shaped implant 1 of the state of the art.

FIG. 1 represents a cube-shaped implant 1 of enlarged size reflecting the state of the art. The open configuration, especially of the faces 2 and vertex areas 4, but also of edges 3, is to be seen as a weak point of such implants 1 because the aneurysm wall in contact with them is particularly prone to rupture. In addition, the insufficient packing density of the implant 1 in the vicinity of said areas 2, 3 and 4 only prevents to a minor extent implants subsequently placed for the purpose of filling the inner hollow space 5 from being expelled again.

Figures 2A, 2B:
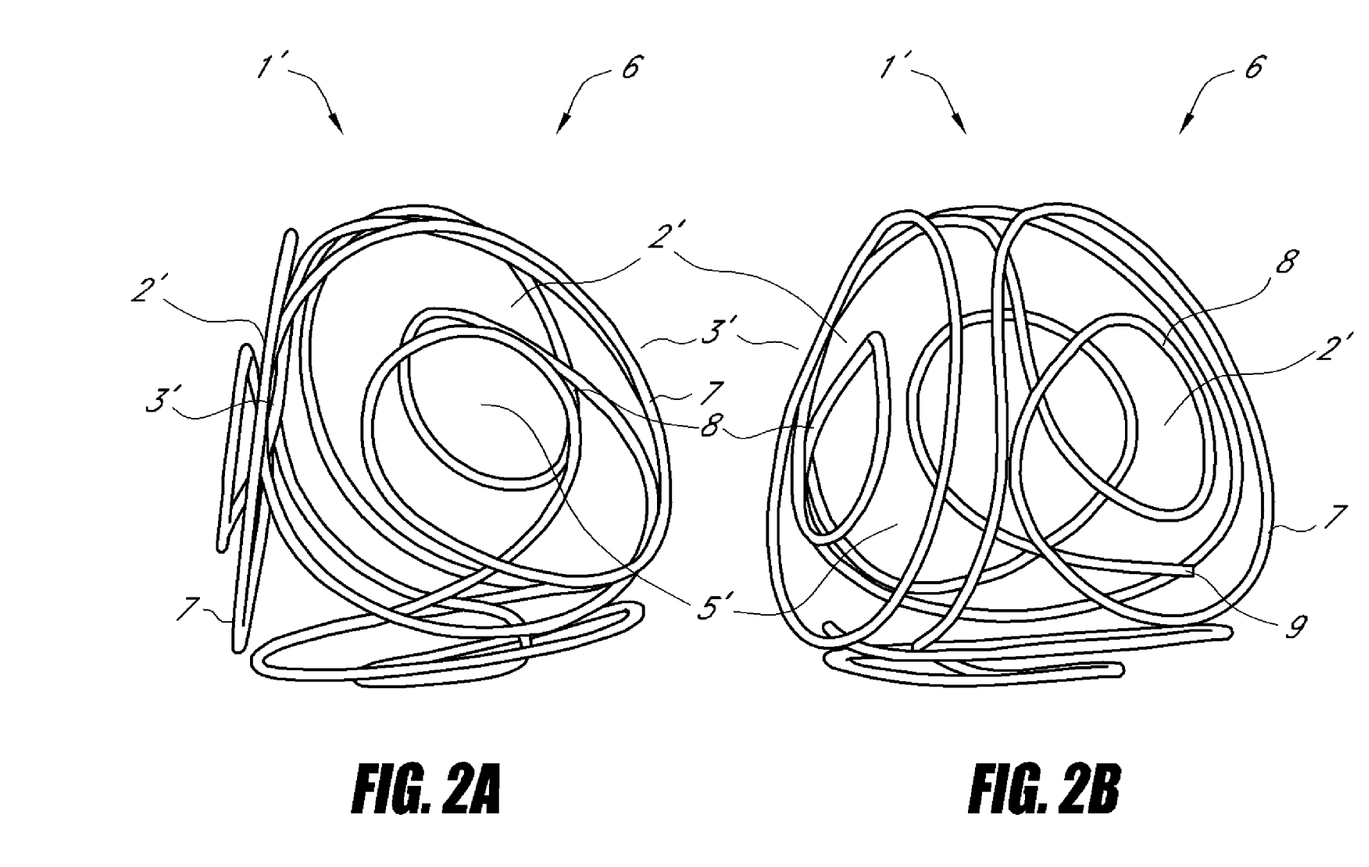
FIGS. 2a and 2b are the enlarged representations of an inventive implant 1' with smaller closed-loops 8 arranged in the tetrahedron faces 2'.

FIG. 2 shows two views 2a and 2b of a tetrahedron-shaped implant 1' according to the invention, said implant having assumed its three-dimensional tetrahedral tertiary structure. The faces 2' of tetrahedron 6 are built up by two uniformly sized large loops 7, two of which in each case being adjacently positioned, with the projections of the large loops 7 extending into the space constituted by the sectional areas of two neighboring large loops 7 each forming the imaginary edges 3' of tetrahedron 6.

In each of faces 2' a loop 8 of smaller size is arranged. By this arrangement the packing density of the tetrahedron 6 in the area of faces 2' is increased, which significantly improves the safety against rupturing dangers to which the adjoining aneurysm wall is exposed when implant segments or further implants are subsequently inserted or placed. The high packing density thus achieved in faces 2' moreover prevents in particular subsequently inserted implant segments or subsequently inserted additional implants meant to fill the inner hollow space 5' from being forced out again through the neck of the aneurysm. For that reason the implant 1' according to the invention is particularly suited as well to the therapeutic occlusion of wide-neck aneurysms the treatment of which, as is known, is especially difficult as a rule.

Besides, the arrangement of the smaller loops 8 slightly raised above the projection plane of the tetrahedron faces 2' formed by the large loops 7 enables the implant 1' to be particularly well secured in the aneurysm, with special reference in this context being made to FIG. 2a.

Filament 9 forming the tetrahedron 6 is a micro-helix having a diameter of 0.26 mm and consisting of a platinum-iridium wire which has a diameter of 60 .mu.m. A nitinol wire extends through the inner hollow space of the micro-helix, said wire being non-detachably connected at the proximal and distal end to filament 9 and due to its elastic biasing force imprinting on the helix 9 the tetrahedral tertiary structure after said helix has been released from the catheter.

Figure 3:
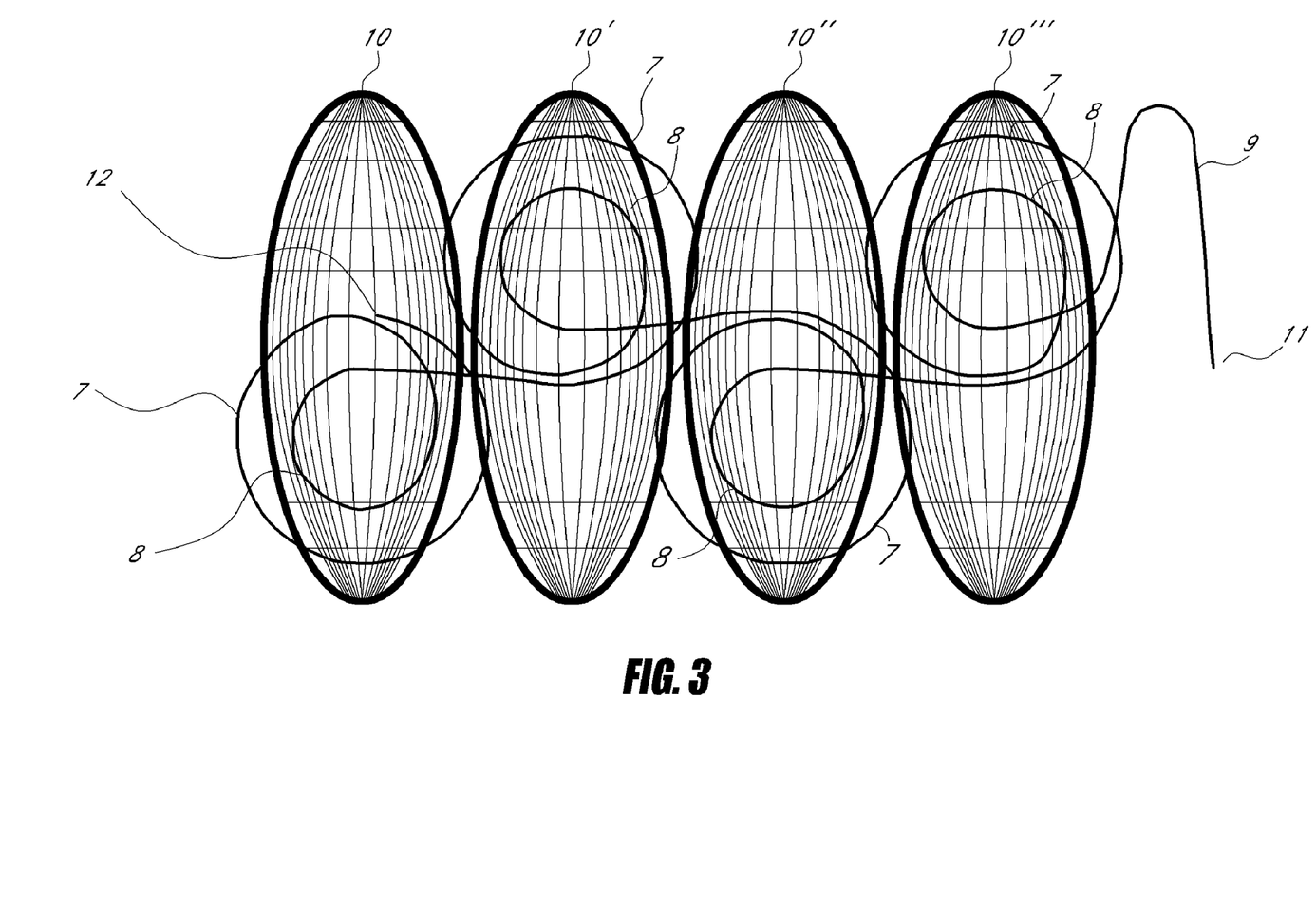
FIG. 3 is the enlarged representation of an inventive implant 1' with smaller closed-loops 8 arranged in the tetrahedron faces 2', shown as development of a ball.

FIG. 3 represents the secondary structure of the tetrahedron shown in FIG. 2 in the form of a development of a ball making use of 4 radial sections 10 to 10'''. The loops 7/8 themselves are of roughly circular shape and having assumed their predetermined spatial configuration form a regular tetrahedron. Along the longitudinal axis of helix 9 the large 7 and the small loops 8 are arranged alternately, with the small loops 8 being placed inside the large loops 7 in the secondary structure. The proximal and the distal ends of filament 9 are identified by reference number 11 and, respectively, 12.

Figure 4A:
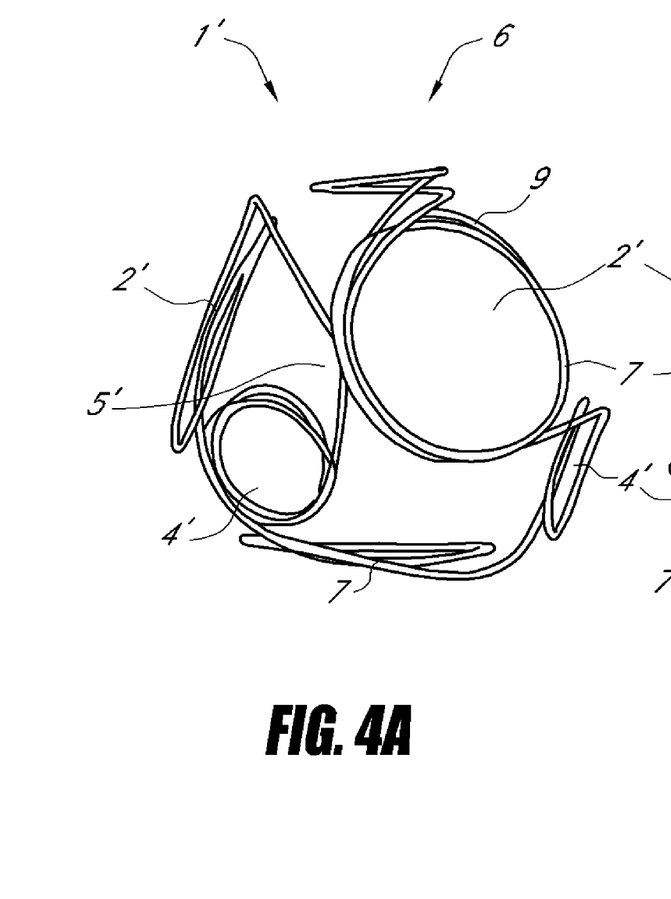
FIGS. 4a and 4b are the enlarged representations of an inventive implant 1' with smaller closed-loops 8 arranged at the vertices 4' of a tetrahedron 6.
Figure 4B:
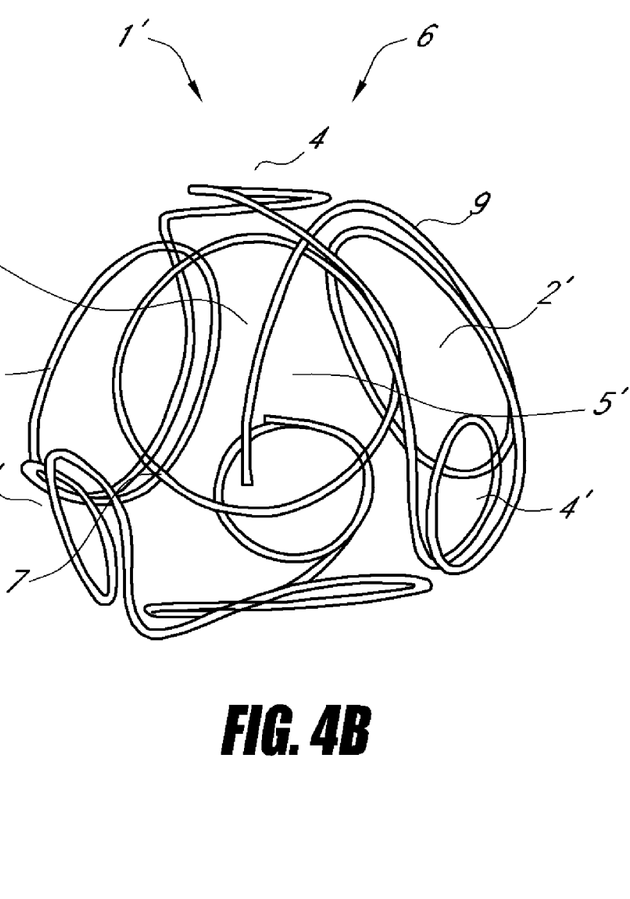

FIG. 4 shows two views 4a and 4b of a tetrahedron-shaped implant 1' according to the invention, said implant having assumed its three-dimensional tertiary structure. The faces 2' of tetrahedron 6 are built up by uniformly sized large loops 7 of which two each are positioned adjacent to each other and thus form by way of their projections the imaginary edges 3' of tetrahedron 6. At the location where the projection of three adjoining large loops 7 each intersects there are the vertices 4' of the tetrahedron, with one smaller sized loop 8 each being arranged at said vertices. Since the smaller loops 8 are arranged below the imaginary points of intersection the tetrahedron 6 in this case has a more rounded shape deviating from an ideal geometric tetrahedron shape. By this arrangement the packing density of the tetrahedron 6 in the area of vertices 4' is increased, which significantly improves the safety against rupturing dangers to which the adjacent aneurysm wall is exposed when implant segments or further implants are subsequently inserted or placed. Aside from this, the rounded tetrahedral shape thus formed will more favorably adapt to the organic structure of aneurysm lumens to be filled than could be accomplished with an ideal geometric tetrahedron. The high packing density thus achieved at vertices 4' moreover prevents in particular implant segments or additional implants subsequently inserted or placed for the purpose of filling the inner hollow space 5' from being forced out again through the neck of the aneurysm.

The helix 9 forming the tetrahedron 6 is a micro-helix having a diameter of 0.26 mm and consisting of a platinum-iridium wire which has a diameter of 60 .mu.m. A polymer thread or a thread made of a nickel-titanium alloy extends through the inner hollow space of the micro-helix, with said thread being fixed at the proximal and distal end of the helix 9 and prevents the helix 9 from being torn off during the placement or repositioning. On the platinum-iridium wire an elastic biasing force has been imprinted which forces it into its preformed tetrahedral configuration as soon as the mechanical constraint caused by the catheter has been omitted. Although the platinum-iridium alloy used has no shape-memory properties it greatly improves the slidability of the helix during placement on account of its excellent supporting characteristics.

Figure 5:
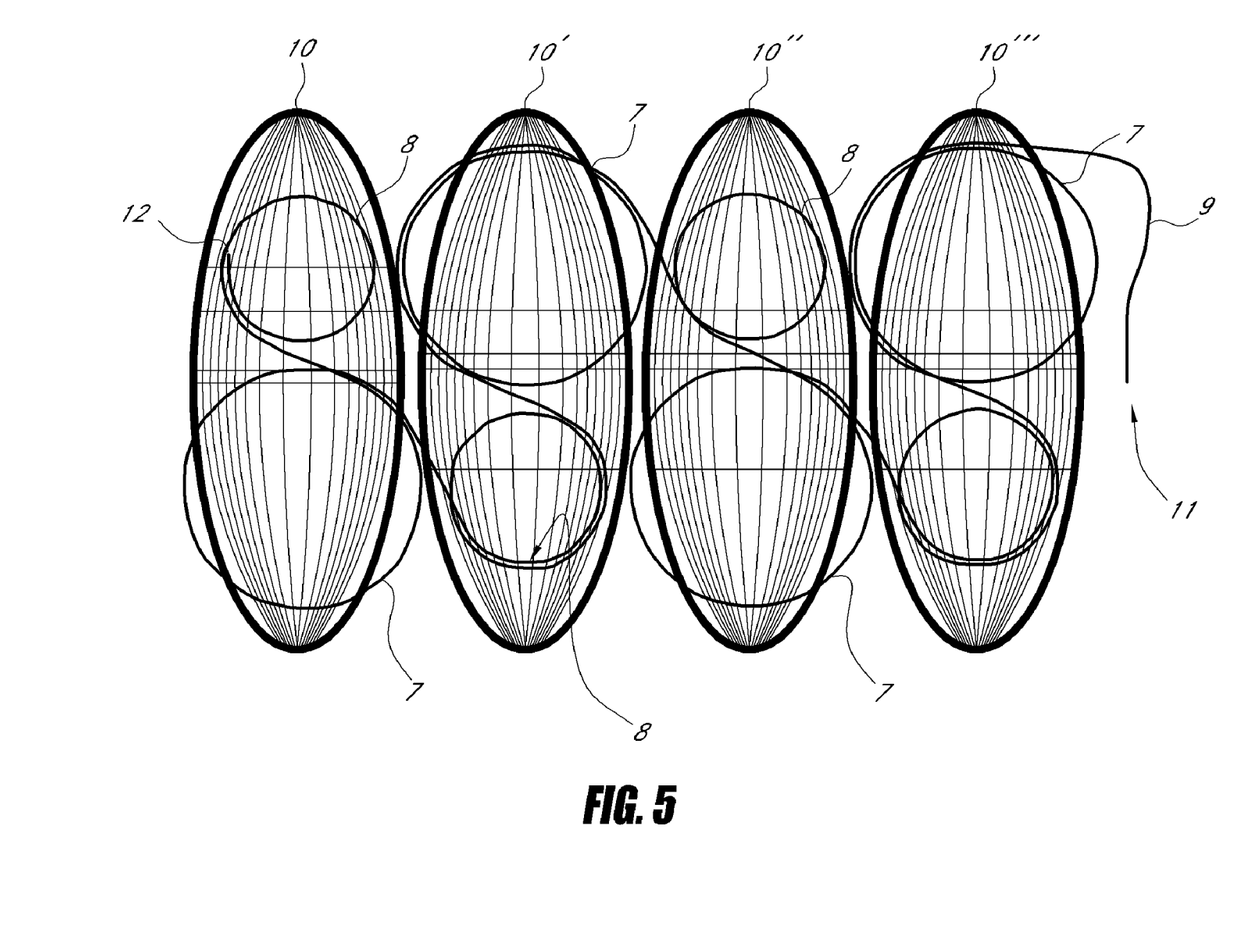
FIG. 5 is the enlarged schematic representation of an inventive implant 1' with smaller closed-loops 8 arranged at the vertices 4' of a tetrahedron 6, shown as development of a ball.

FIG. 5 by way of 4 radial sections 10 to 10''' represents the secondary structure of the tetrahedron shown in FIG. 4 in the form of the development of a ball. The loops 7/8 themselves are of roughly circular shape and having assumed their predetermined spatial configuration form a regular tetrahedron. Along the longitudinal axis of helix 9 the large 7 and the small loops 8 are arranged alternately, with the small loops 8 being placed between the large loops 7. The proximal and the distal ends of helix 9 are identified by reference number 11 and, respectively, 12.

Figure 6:
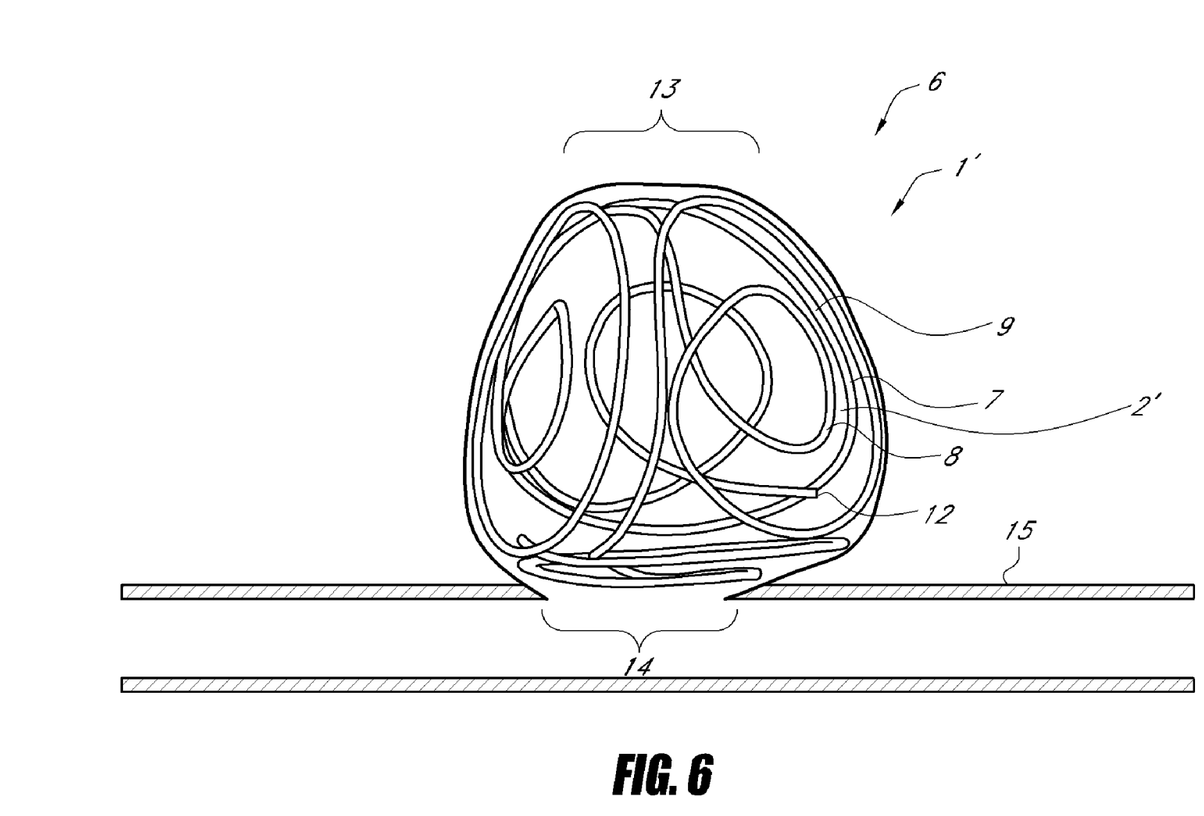
FIG. 6 is the enlarged vertical section of the inventive implant 1' positioned in an aciniform aneurysm 13.

In FIG. 6 an implant 1' according to the invention is illustrated that is placed into an aciniform aneurysm 13, said implant forming into a tetrahedron 6 as tertiary structure. By arranging the smaller loops 8 in the area of the faces 2' of the tetrahedron 6 built up by the large loops 7 a higher packing density of the tetrahedron faces 2' is achieved. This not only reduces the danger of a wall rupture but also and in particular prevents additionally inserted implants (not shown here) from exiting through the neck of the aneurysm 14. This configuration even enables aneurysms exhibiting medium-sized necks 14 as illustrated here to be occluded without having to employ stents. It is particularly expedient here if the implant 1' as shown is positioned in such a way that one of the tightly packed face areas 2' of the tetrahedron 6 is situated at or above the aneurysm neck 14.

The tetrahedral tertiary structure is excellently suited for the occlusion of large aneurysms, for example of an aneurysm 13 as shown here having a therapeutic dimension of 10 mm in diameter. Since the tetrahedron 6 has a diameter of 12 mm it secures itself firmly inside the aneurysm 13 during placement when forming into its tertiary structure such that the tension thus built up prevents it from slipping out of the aneurysm 13. Such an "oversizing" offers advantages particularly for the treatment of wide-neck aneurysms because customary implants are not sufficiently secured inside of them to make sure they cannot exit or be expelled.

With the help of a micro-catheter the implant 1' with the distal portion 12 of the helix 9 in front was moved through the blood vessel 15 into the aneurysm 13 where, when discharged from the catheter, it assumed the illustrated three-dimensional tertiary structure on account of a mixed stress- and temperature-induced martensitic transformation of the nitinol wire accommodated in the micro-helix 9 consisting of a platinum-iridium alloy. After checking the correct positioning under radiographic control by employing customary state-of-the-art methods the implant was detached electrolytically from the insertion aid designed in the form of a guide wire. For this purpose and with the aid of a source of electrical power a voltage was applied for a period of 0.1 to 20 minutes to the cathode positioned on the body surface and to the implant 1' acting as anode and being placed in the aneurysm 13 to be occluded. Applying this voltage resulted in the implant 1' becoming electrolytically detached due to electrolytic corrosion taking place at the electrolytically corrodible location in the severance module arranged between the guide wire and the filament 9. Said severance module is of particularly robust design and has a relatively large diameter of 100 .mu.m to yield a high margin of safety preventing kinking or buckling when the implant 1 is positioned. Finally, the guide wire was retracted into the catheter and then removed from the system together with the catheter.

Figure 7:
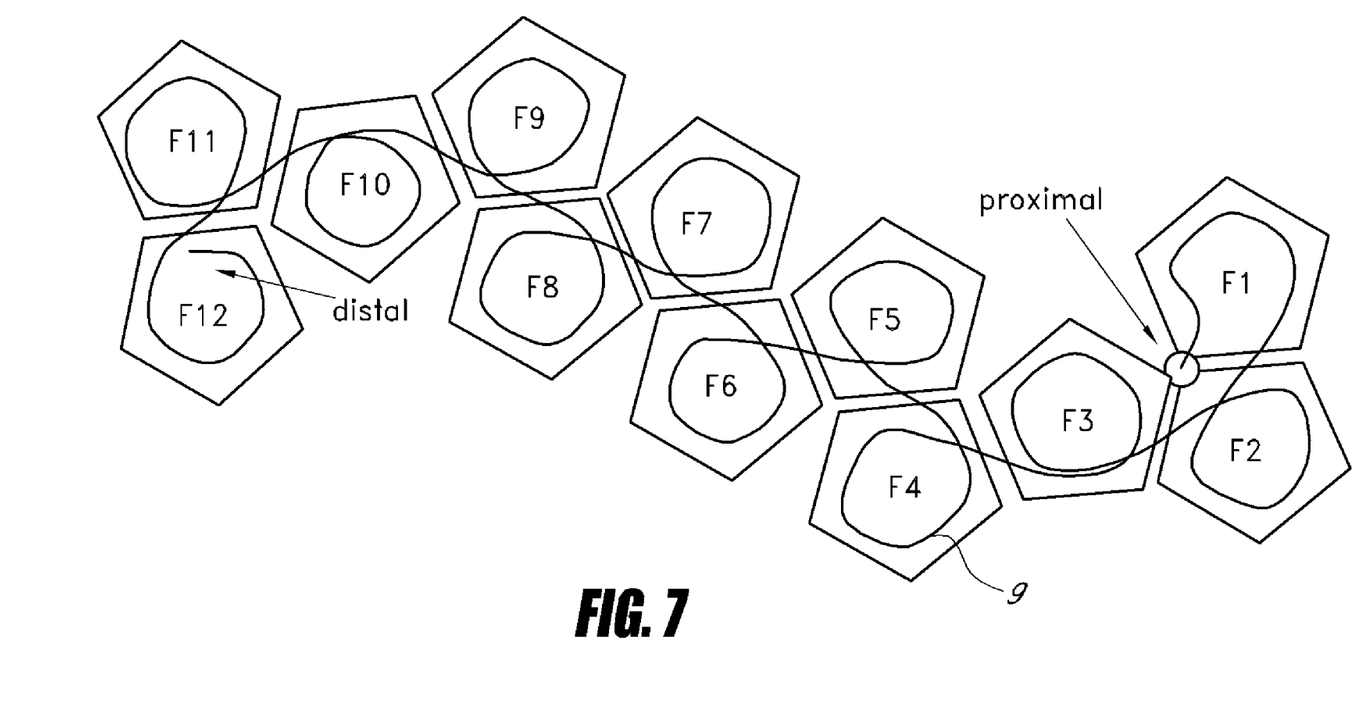
FIG. 7 is the schematic representation of a development of an inventive implant in the form of a pentagonal dodecahedron.

FIG. 7 is a schematic view of the development of a pentagonal dodecahedron and the extension of a micro-helix 9 designed to form into a pentagonal dodecahedron. The individual faces F1 to F12 of the polyhedron are defined by the loops of the micro-helix. In this case the distal end of the micro-helix 9 is located on a face F12 whereas the proximal end enters the body at a vertex or corner point between F1/F2/F3.

Figure 8:
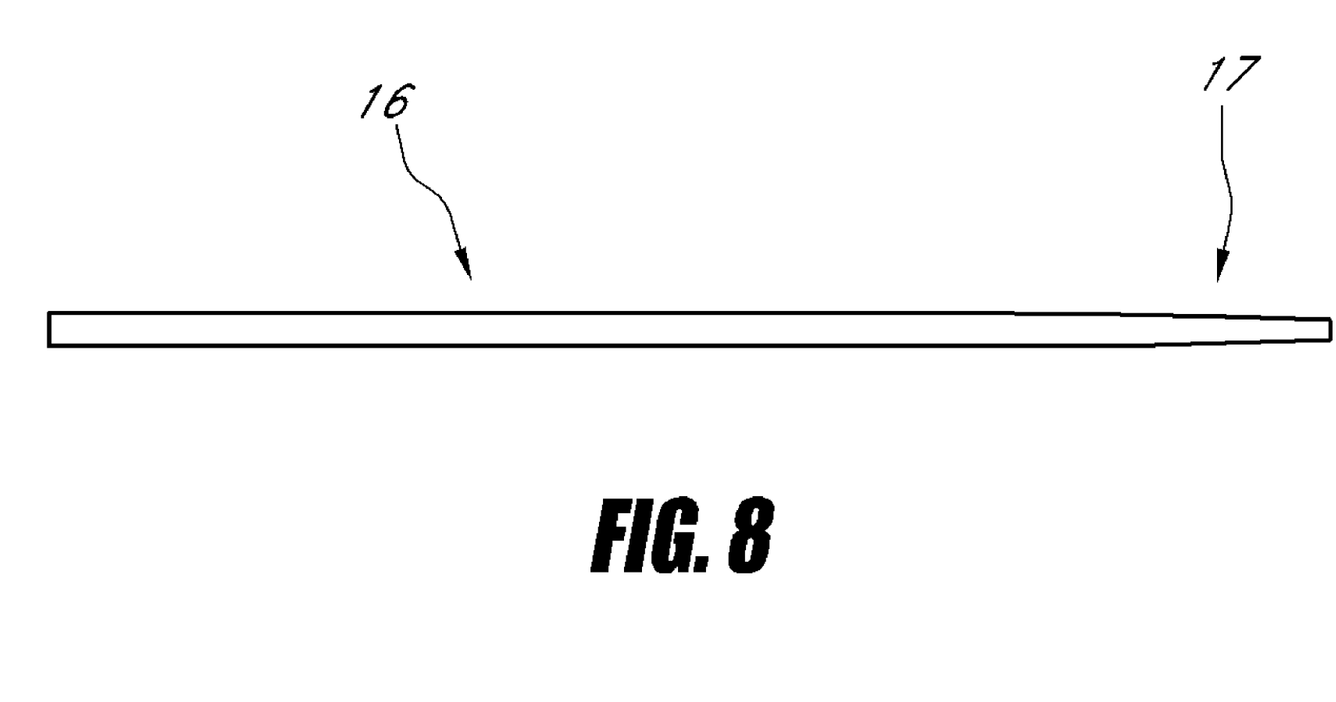
FIG. 8 shows the taper provided in the distal end area of a filamentous shaping element.

FIG. 8 eventually shows as schematic representation the tapered portion of the distal end 17 of a filamentous shaping element 16 reducing to approx. 50% of the diameter.

What is claimed is:

1. A medical implant comprising:
   an elongated helix;
   at least one part of the helix preformed to define a secondary structure comprising a first face loop, a second face loop, a third face loop and a fourth face loop, the first, second, third and fourth face loops of substantially identical size;
   said secondary structure biased to form a polyhedral tertiary structure, the polyhedral tertiary structure comprising a polyhedron, wherein the faces of the polyhedron are built up by the first face loop, the second face loop, the third face loop and the fourth face loop; and
   the polyhedron further comprising at least one additional loop disposed on one of the groups consisting of a polyhedron edge and a polyhedron vertex, the at least one additional loop configured for reducing the risk of damage at the placement site,
   wherein the at least one additional loop is smaller than the first face loop.

2. The medical implant according to claim 1, wherein the additional loop is arranged near the first face loop of the polyhedron.

3. The medical implant according to claim 1, wherein the at least one additional loop is a closed loop.

4. The medical implant according to claim 1, further comprising multiple additional loops coplanar to the plane of at least one of the first, second and third loops of the polyhedron, wherein each additional loop is smaller than its corresponding larger face loop forming the polyhedron face.

5. The medical implant according to claim 1, wherein the polyhedron comprises a smaller additional loop arranged in each of the polyhedron faces which are formed by the larger loops.

6. The medical implant according to claim 1, further comprising a microcoil having a lumen which is closed at least at a distal end thereof.

7. The medical implant according to claim 1, wherein at least one of the wires forming the elongated helix comprises one of a platinum-iridium and platinum-tungsten alloy having shape memory properties.

8. The medical implant according to claim 1, wherein a filamentous shaping element made of a metal alloy having shape memory properties passes through the elongated helix along a longitudinal axis thereof.

9. The medical implant according to claim 8, further comprising a filamentous retaining element made of a polymer material or a metal wire without shape memory properties passes elongated helix along a longitudinal axis thereof.

10. The medical implant according to claim 1 further comprising at least one severance module provided with an electrolytically corrodible location which is arranged in the elongated helix proximally to a portion thereof forming the polyhedron.

11. The medical implant according to claim 1 in combination with a catheter and an insertion aid which is detachably connected to a proximal end of the implant.

* * * * *